United States Patent
Yu

(10) Patent No.: US 7,999,063 B2
(45) Date of Patent: *Aug. 16, 2011

(54) POLYQUATERNIUM-1 SYNTHESIS METHODS AND ASSOCIATED FORMULATIONS

(75) Inventor: Zhi-Jian Yu, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/429,134

(22) Filed: Apr. 23, 2009

(65) Prior Publication Data

US 2009/0203795 A1    Aug. 13, 2009

Related U.S. Application Data

(63) Continuation-in-part of application No. 11/609,422, filed on Apr. 17, 2007, now Pat. No. 7,705,112.

(51) Int. Cl.
*C08G 67/00* (2006.01)
*C08F 14/14* (2006.01)
*A61K 31/785* (2006.01)

(52) U.S. Cl. ............... 528/392; 424/78.04; 514/642

(58) Field of Classification Search ............... 528/392; 424/78.04; 514/642
See application file for complete search history.

(56) References Cited

U.S. PATENT DOCUMENTS

| | | | |
|---|---|---|---|
| 3,874,870 A | 4/1975 | Green et al. | |
| 3,931,319 A | 1/1976 | Green et al. | |
| 4,016,128 A | 4/1977 | Serlin et al. | |
| 4,027,020 A | 5/1977 | Green et al. | |
| 4,525,346 A * | 6/1985 | Stark | 424/78.04 |
| 4,734,277 A | 3/1988 | Login | |
| 4,758,595 A | 7/1988 | Ogunbiyi et al. | |
| 5,512,597 A * | 4/1996 | Kyba et al. | 514/642 |
| 6,051,611 A * | 4/2000 | Kyba et al. | 514/642 |
| 6,528,048 B1 * | 3/2003 | Koike et al. | 424/78.17 |

OTHER PUBLICATIONS

Registry Engtry for polyquaternium-1.*

* cited by examiner

*Primary Examiner* — Milton I Cano
*Assistant Examiner* — Brieann R Fink

(57) ABSTRACT

A multipurpose solution for contact lens care, comprising: an aqueous liquid medium; a quaternary ammonium polymer having an average molecular weight as determined by the proton NMR method of at least 22 k, and methods for making.

13 Claims, 9 Drawing Sheets

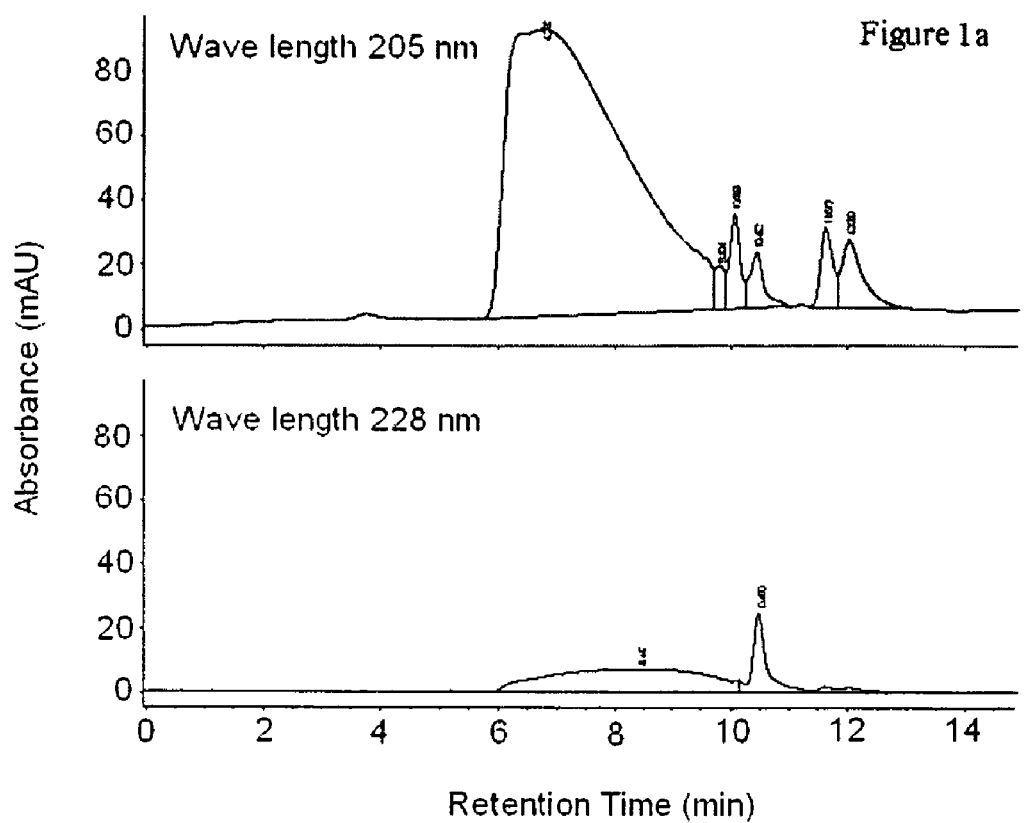

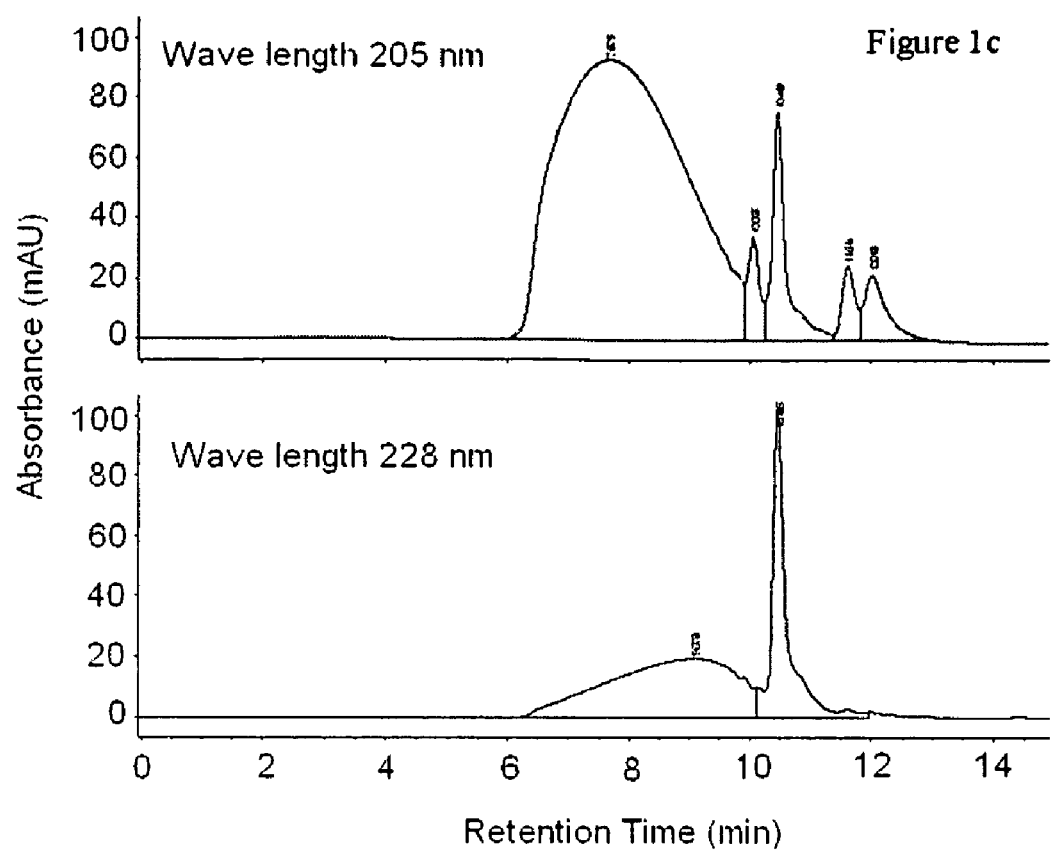

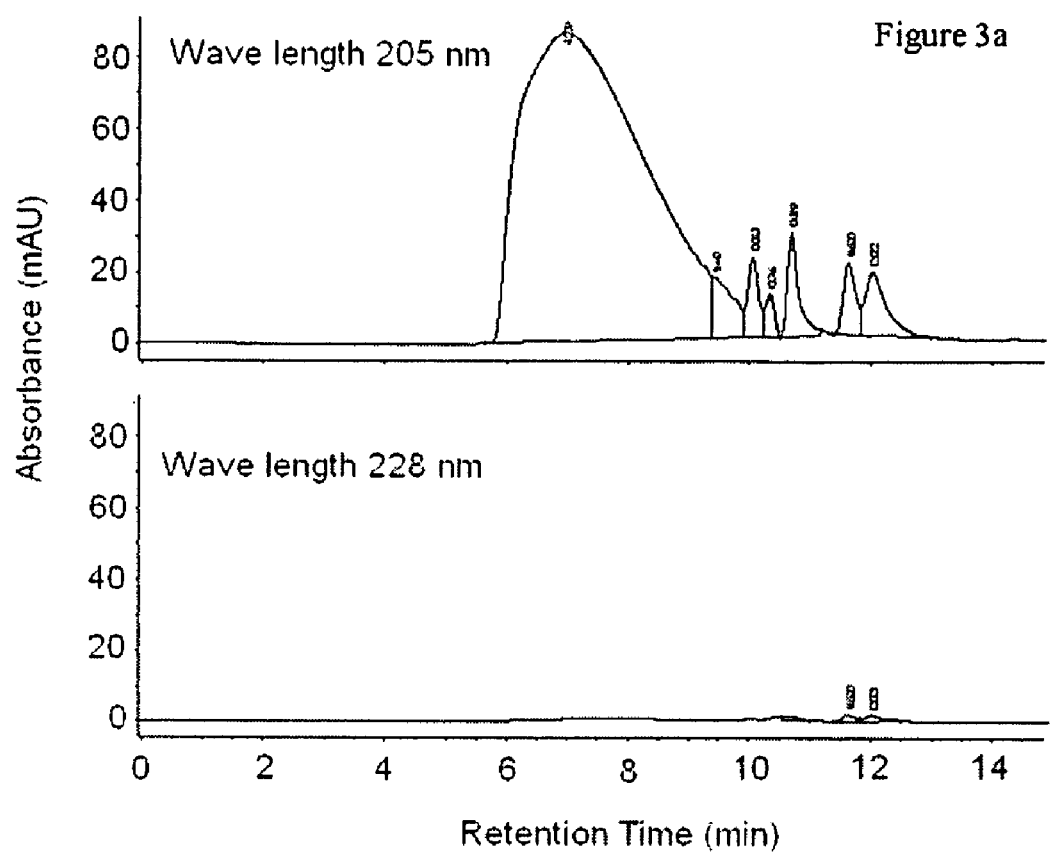

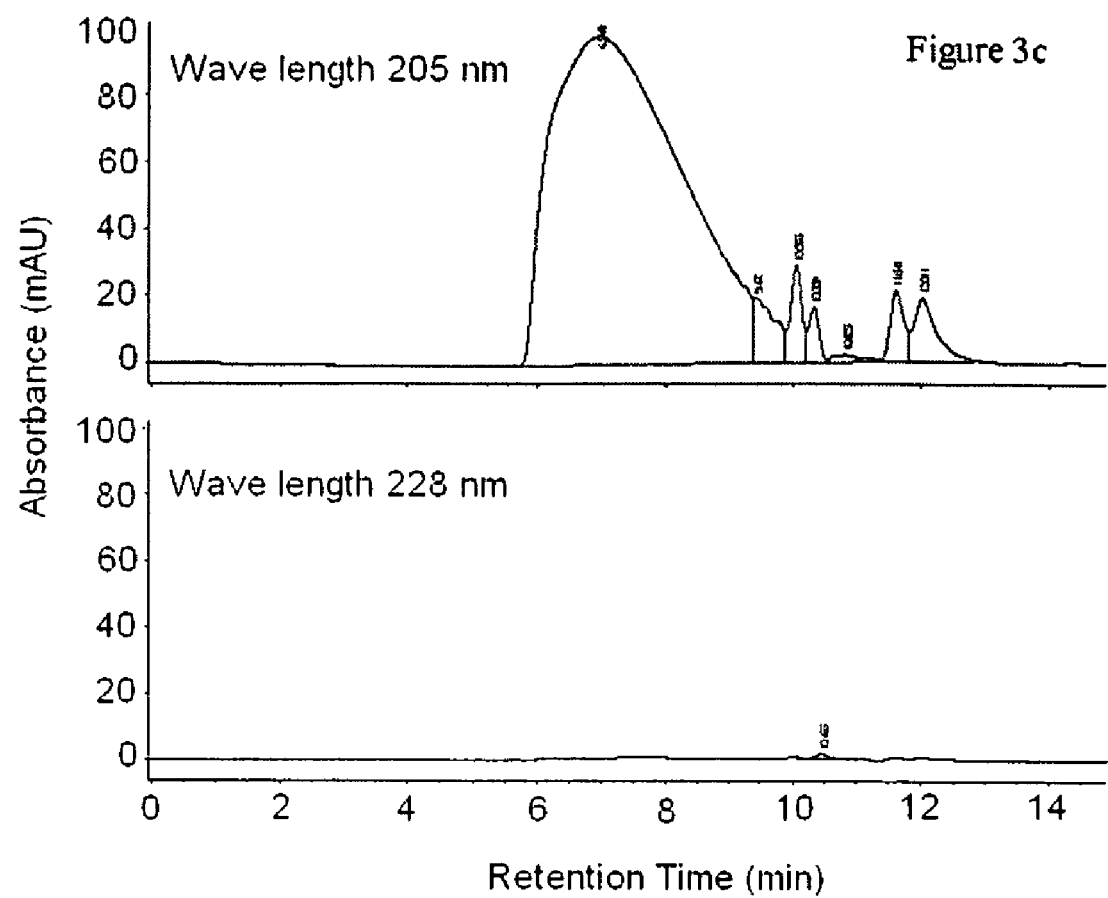

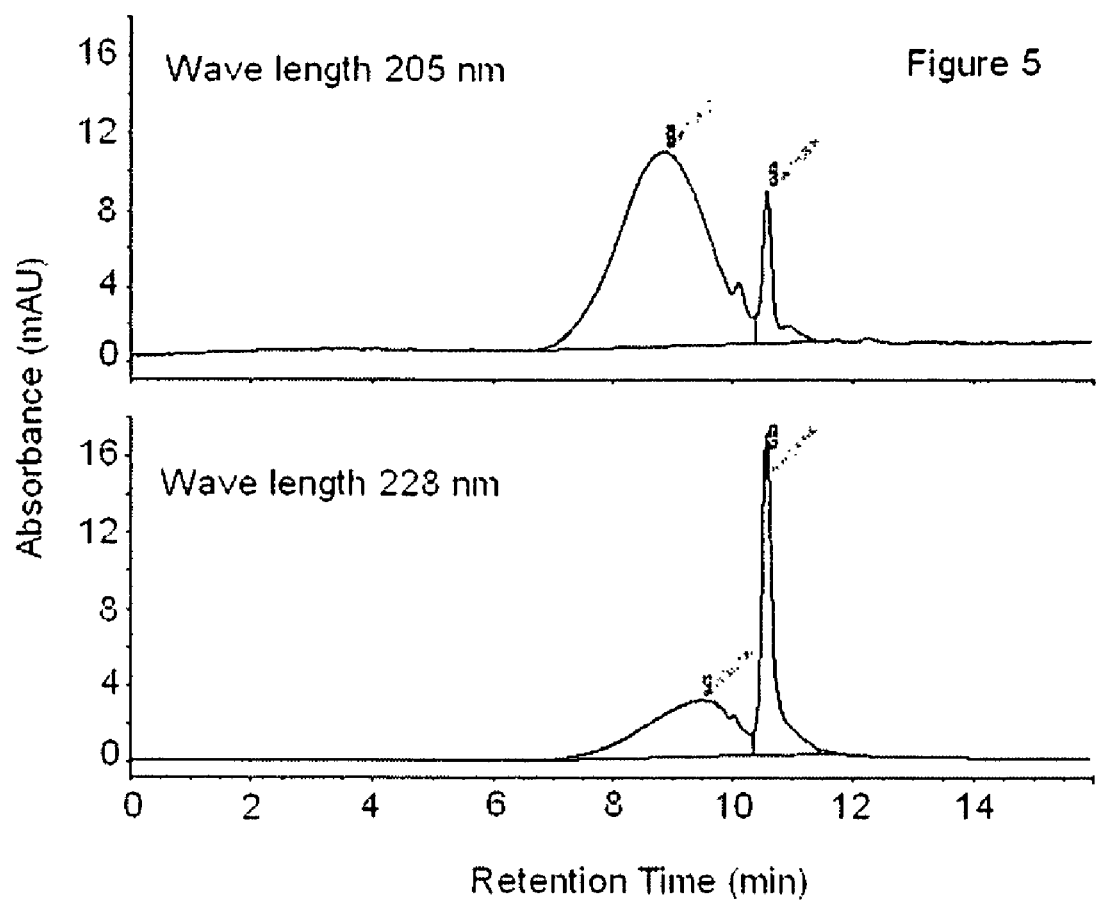

POLYQUATERNIUM-1 SYNTHESIS METHODS AND ASSOCIATED FORMULATIONS

RELATED CASES

This application is a continuation-in-part application of U.S. patent application Ser. No. 11/609,422, entitled Polyquaternium-1 Synthesis Methods, filed Apr. 17, 2007, now U.S. Pat. No. 7,705,112, which is incorporated herein in its entirety.

BACKGROUND OF THE INVENTION

1. Field of the Invention

The present embodiments relate to an improved method of synthesizing polyquaternium-1 and related molecules for use as antimicrobial agents in contact lens solutions.

2. Description of the Related Art

Quaternary ammonium polymers in which the ammonium moieties are part of the linear polymeric chains have been used as antimicrobial agents in several industries. Polyquaternium-1 (PQ1) is a polymeric quaternary ammonium antimicrobial agent that has been used, for example, in preserving ophthalmic compositions and disinfecting contact lenses. PQ1 is effective against bacteria, algae and fungi. Its chemical name is Poly[(dimethyliminio)-2-butene-1,4-diyl chloride], $\alpha$-[4-[tris(2-hydroxyethyl) ammonio]-2-butenyl]-$\omega$-[tris(2-hydroxyethyl)ammonio]-dichloride.

U.S. Pat. No. 3,931,319, which is hereby incorporated in its entirety by reference, describes a two-step method for PQ1 synthesis which requires a high reaction temperature. This leads to significant degradation of the target molecule into impurities from which the desired PQ1 is difficult to separate.

U.S. Pat. No. 4,027,020, which is hereby incorporated in its entirety by reference, describes a procedure for polyquaternium-1 synthesis which results in less degradation of the resulting PQ1 than the method described in U.S. Pat. No. 3,931,319 but still produces a rather low yield. The procedure disclosed in U.S. Pat. No. 4,027,020 entails mixing 1,4-bis-dimethylamino-2-butene with triethanolamine (TEA), the molar ratio of the 1,4-bis-dimethylamino-2-butene to the TEA amine being from 2:1 to 30:1 followed by the addition of 1,4-dichloro-butene to the mixture in a molar amount equal to the sum of the molar amount of the 1,4-bis-dimethylamino-2-butene plus one-half the molar amount of TEA. The reaction time is 1-10 hours.

A major weakness of the method taught in U.S. Pat. No. 4,027,020 is that the TEA end-capping efficiency is low. As such, the final product contains a significant amount of polymers with no end caps or polymers end-capped with groups other than TEA. These malformed polymers are difficult to separate from polyquaternium-1 because of the similarity in the main chain of the polymeric molecules. Degraded or malformed polymers of PQ1 have reduced anti-bacterial efficacy and cannot substitute for PQ1 in clinical use.

Soft contact lenses usually attract and accumulate quaternary ammonium antimicrobial agents during the lens cleaning/disinfecting/storing cycles. The accumulated antimicrobial agents in the lens are subsequence released once the lens is put in to the eye, causing the contact lens wearer's eye irritation. An effective way to reduce the antimicrobial agents lens uptake is to use low concentration antimicrobial agents. This requires that the antimicrobial agents are of high efficacy. Another way to reduce the eye irritation is to use less cytotoxic antimicrobial agents in MPS.

SUMMARY OF THE INVENTION

One object of the invention is to provide a multipurpose solution for contact lens care, comprising: an aqueous liquid medium; and from about 0.00001% to about 0.01% w/w of a quaternary ammonium polymer having a number average molecular weight of at least 22 k.

Another object of the invention is to provide a multipurpose solution for contact lens care, comprising: an aqueous liquid medium; and from about 0.00001% to about 0.01% w/w of PQ1 obtained by a process of:

a) mixing 1,4-bis-dimethylamino-2-butene, water, a first portion of triethanolamine and a first portion of acid;

b) adding a 1,4-dihalo-2-butene and heating the reaction mixture;

c) adding a second portion of triethanolamine and a second portion of acid, and d) isolating Polyquaternium-1 having an average molecular weight as determined by the proton NMR method of 22 k or more, at a yield of at least about 50%.

BRIEF DESCRIPTION OF THE DRAWINGS

FIG. 5 shows the GPC chromatograms for the products of the reaction as described in comparative example 2.

DETAILED DESCRIPTION

Figure 1B:
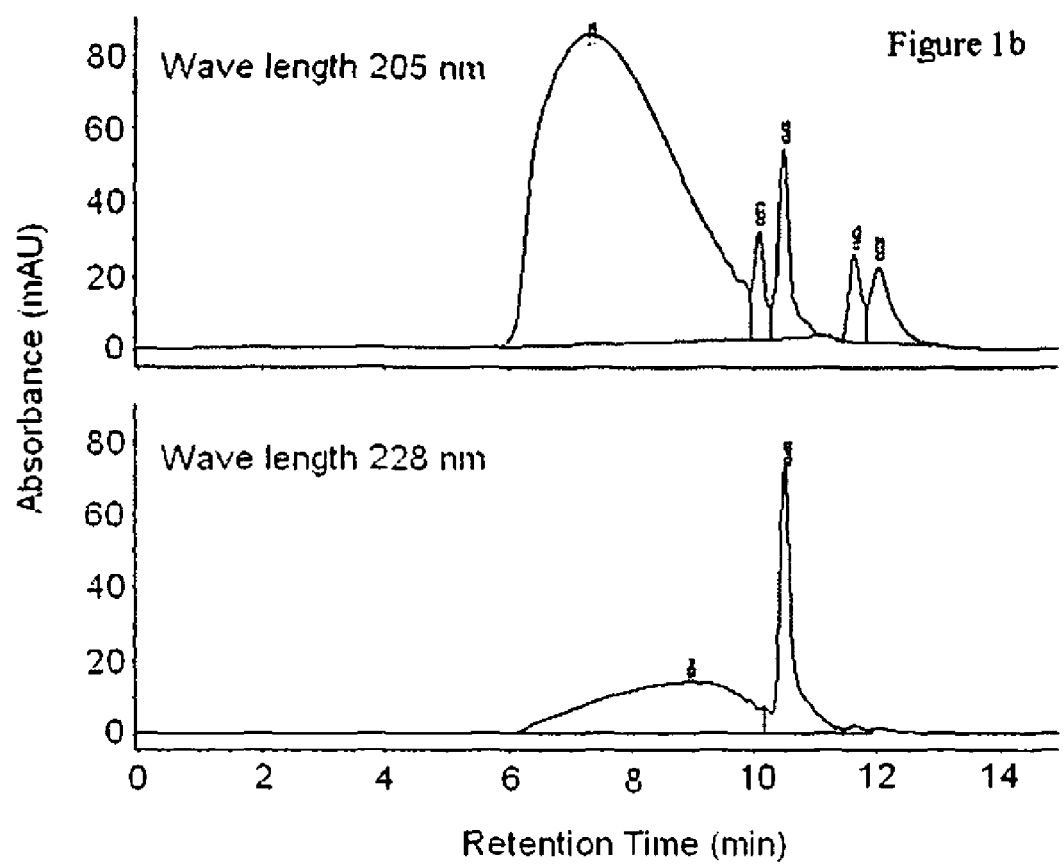
FIG. 1 shows GPC chromatograms for the products of comparative example 1 having no acid added to the reaction mixture.

Various multipurpose lens care solutions have been developed over the years in an attempt to minimize pathogens and deposits on contact lenses. These contact lens solutions typically include anti-microbial substances as well as cleaning (active against both lipids and proteins), wetting, conditioning, and other agents for the disinfection and cleaning of contact lenses during storage after wear. So-called, multipurpose solutions (MPS) can disinfect and clean without harming the eye or lens in addition to wetting.

It has been discovered that high molecular weight PQ1, which may be manufactured in accordance with aspects of the present invention, is more efficacious in killing microorganisms and less toxic to the eye than low molecular weight PQ1.

The present embodiments relate to improved methods for the synthesis of high molecular weight quaternary ammonium polymers by adding triethanolamine (TEA) in two separate stages. The method involves addition of acid to the reaction mixture in separate stages as well. The overall method prevents impurity generation and the degradation of synthetic quaternary ammonium polymers, including PQ1, during the reaction. Recent experiments have shown that past methods of synthesizing quaternary ammonium polymers are not as efficient as originally thought. This is due in party to the fact that too little TEA was used in the reaction admixture.

Regardless of the molar ratio of TEA used, PQ1 synthesized by conventional methods described in U.S. Pat. Nos. 4,027,020 and 3,931,319 invariably result in significant PQ1 degradation during the reaction process. The molecular structure of PQ1 can be expressed as:

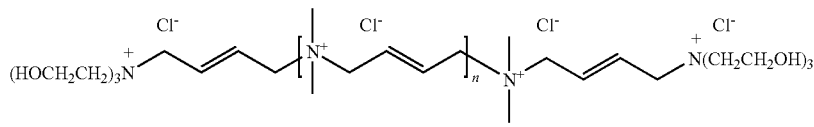

The majority of the degraded molecules are:

A) $(HOC_2H_4)_3NCH_2CH=CHCH_2(N(CH_3)_2CH_2CH=CHCH_2)_{n-1}N(CH_3)_2$ and

B) $H_2C=CHCH=CH(N(CH_3)_2CH_2CH=CHCH_2)_m N(HOC_2H_4OH)_3$.

These degraded molecules are difficult to separate from PQ1, since both are polymeric quaternary amine-based like PQ1. Degraded or malformed polymers of PQ1 have reduced anti-bacterial efficacy and cannot be substituted for PQ1 in clinical use.

Nucleophilic substitution reactions involving alkyl halides are well known in the literature. A nucleophilic agent is a Lewis base which can donate an unshared pair of electrons to form a new covalent bond. $(HOC_2H_4)_3NH^+$ is a Lewis acid and, therefore, does not normally react with ClCH2CH=CHCH2(N(CH3)2CH2CH=CHCH2)n-1N(CH3)2CH2CH=CHCH2Cl in the end-capping step of the reaction to form PQ1. Therefore, the current literature view is that acids should be avoided in the nucleophic reaction of the present embodiments for fear that acid could convert the nucleophilic agent $(HOC_2H_4)_3N$ into inactive $(HOC_2H_4)_3NH^+$ ions. However, contrary to the current literature view, the present embodiments relate to a synthesis wherein the addition of acid to the reaction mixture does not prevent the TEA end-capping reaction.

U.S. patent application Ser. No. 11/609,422, describes an acid catalyzed method for PQ1 synthesis. In this method all the raw materials, such as 1,4-bis-dimethylamino-2-butene (DA), TEA, 1,4-dichloro-2-butene (DCB) and an acid (e.g., HCl), mixed together directly. The following two reactions start simultaneously:

In the methods of the prior art that do not include the addition of acid to the reaction mixture, when 1,4-bis-dimethylamino-2-butene, triethanolamine and water are mixed, the hydroxide concentration is very high, usually greater than about $10^{-3}$ M. Since the nucleophilicity of hydroxide is much stronger than that of TEA and 1,4-bis-dimethylamino-2-butene, large amounts of 1,4-dihalo-2-butene are attacked by hydroxide in the prior art methods, resulting in $HOCH_2CH=CHCH_2Cl$ or $HOCH_2CH=CHCH_2OH$. As discussed below, hydroxide also competes with TEA in the end-capping reaction of PQ1, resulting low yield and high impurities for PQ1. Therefore, in the present embodiments the presence of acid is advantageous in the reaction admixture to prevent PQ1 degradation, improve the reaction yield and reduce product impurity, regardless of the molar ratio of 1,4-bis-dimethylamino-2-butene to triethanolamine.

Significant PQ1 degradation during the synthesis process can be prevented by adding acid to the reaction admixture. Addition of acid greatly reduces the formation of degraded impurities and increases the yield of PQ1 in the reaction.

In the present method, the molar amount of DCB should be: (1) enough to cap the two ends of the product of Reaction 1, and (2) maintain a certain amount of excess, so that the PQ1 chain-length extension of Reaction 1 is fast enough to avoid hydrolysis of the end cap group $—CH_2Cl$ to $—CH_2OH$. A portion of the TEA is added after Reaction 1 is completed so that Reaction 2 can take place before the end caped $—CH_2Cl$ groups are hydrolyzed.

Since DCB is a very toxic material, the excess amount must be neutralized by TEA by the end of the reaction. This is usually achieved by adding a large excess of TEA to the Reaction 1

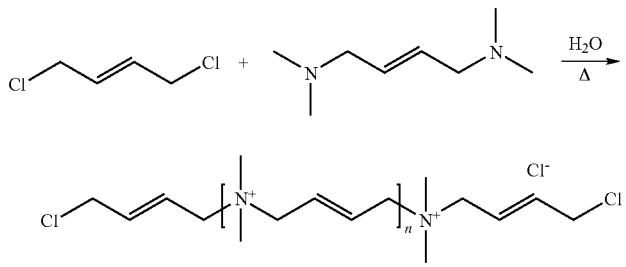

Reaction 2

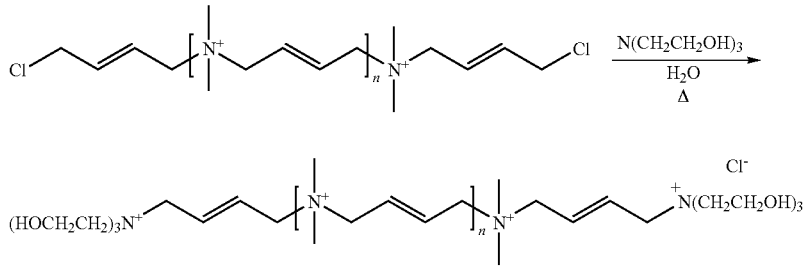

reaction mixture. However, a problem arises because that the molecular weight of the resulting PQ1 is not as high as desired. This is because the existence of a large excess of TEA also accelerates the end group capping Reaction 2, and so the antimicrobial activity of the product is reduced. Whenever a TEA molecule reacts with the —$CH_2Cl$ group of the product in Reaction 1, that side of the PQ1 chain stops chain growth.

According to the present invention, if the total amount of TEA is divided into two parts, so that one part is added before Reaction 1, and the second part is added 10 minutes to 8 hours after the process begins, the product's molecular weight is much higher than by using a one-step TEA addition. In this way the hydrolysis reaction of the end cap group —$CH_2Cl$ can be avoided but the excess amount of DCB can still be neutralized.

The synthesis of PQ1 described herein involves a 1,4-dihalo-2-butene including, for example, 1,4-dichloro-2-butene, 1,4-difluoro-2-butene, 1,4-dibromo-2-butene, and/or 1,4-diiodo-2-butene. In a preferred embodiment, the 1,4-dihalo-2-butene is 1,4-dichloro-2-butene.

The following examples are provided for illustrative purposes only, and are in no way intended to limit the scope of the present invention.

COMPARATIVE EXAMPLE 1

PQ1 was synthesized as described in U.S. Pat. No. 4,027,020 using a reactant admixture of 1,4-bis-dimethylamino-2-butene with TEA in which the molar ratio of 1,4-bis-dimethylamino-2-butene to TEA was about 5:1 and the molar ratio of 1,4-dichloro-butene to 1,4-bis-dimethylamino-2-butene was about 1.1:1. The reaction was carried out at 65° C. The proton NMR spectra were obtained for the final product after it was purified with ultrafiltration. The results are summarized in Table 1, where the peaks at the chemical shift of 6.5 ppm and 3.7 ppm are for vinyl protons in repeating units and allylic protons adjacent to the nitrogen in the ending group of the PQ1 molecules, respectively.

Table 1 one shows that the TEA end-capping efficiency is low in 6 hours reaction at which the reaction was believed by the authors of the U.S. Pat. No. 4,027,020 patent to be complete. The reaction time was then extended from 6 to 10 hours and the results show that the amount of proton in the end cap group of the polymers is still increasing. Therefore, the end-capping reaction for PQ1 synthesis is not completed at 6 hours and is approximately only 71% complete.

TABLE 1

| Reaction Time | Peak area at 6.5 ppm Chemical shift | Peak area at 3.7 ppm Chemical shift |
| --- | --- | --- |
| 6 hours | 1.000 | 0.0343 |
| 10 hours | 1.000 | 0.0481 |

The low end-capping efficiency is due to the low amount of TEA in the reactant admixture. The low TEA concentration in the reaction mixture slows down its kinetic reaction rate with $ClCH_2CH=CHCH_2(N(CH_3)_2CH_2CH=CHCH_2)_n$ $CH_2CH=CHCH_2Cl$. Meanwhile, water molecules and hydroxide ions (OH—) in the solution may compete with TEA to form $OHCH_2CH=CHCH_2(N(CH_3)_2CH_2CH=CHCH_2)_nCH_2CH=CHCH_2OH$.

FIGS. 1a, 1b and 1c represent the GPC chromatograms for PQ1 synthesized with admixtures of 1 mole of 1,4-bis-dimethylamino-2-butene, 0.9 moles of TEA, and 1.15 moles of 1,4-dichlo-butene at 65° C. at 2, 6 and 10 hours respectively.

A GPC-HPLC chromatograph was used to trace the PQ1 molecular size. The experimental conditions were: an aqueous solution of 0.045 M $KH_2PO_4$, 0.45% NaCl and 9.1% $CH_3CN$ as a mobile phase in a Phenomenex BioSep-SEC-S 2000 column and an Agilent 1100 Series HPLC system equipped with PDA detector. PQ1 molecules have an absorbance peak at 205 nm but do not have an absorbance peak at 228 nm. However, the degraded molecules have an absorbance maximum at 228 nm. Therefore the detection wavelengths of 205 nm and 228 nm are used to trace PQ1 and its degradated segments, respectively, during the reaction process.

The broad peak shown in FIGS. 1a, 1b and 1c which ranges from 6 to 10 minutes retention time represents polymeric molecules of PQ1 and its degraded products. The larger the polymeric molecules, the shorter the retention time will be. The water solvent peak locates at about 10 minutes. The peaks beyond 10 minutes represent non-polymeric small molecules of either the reactants or bi-products.

Figure 2:
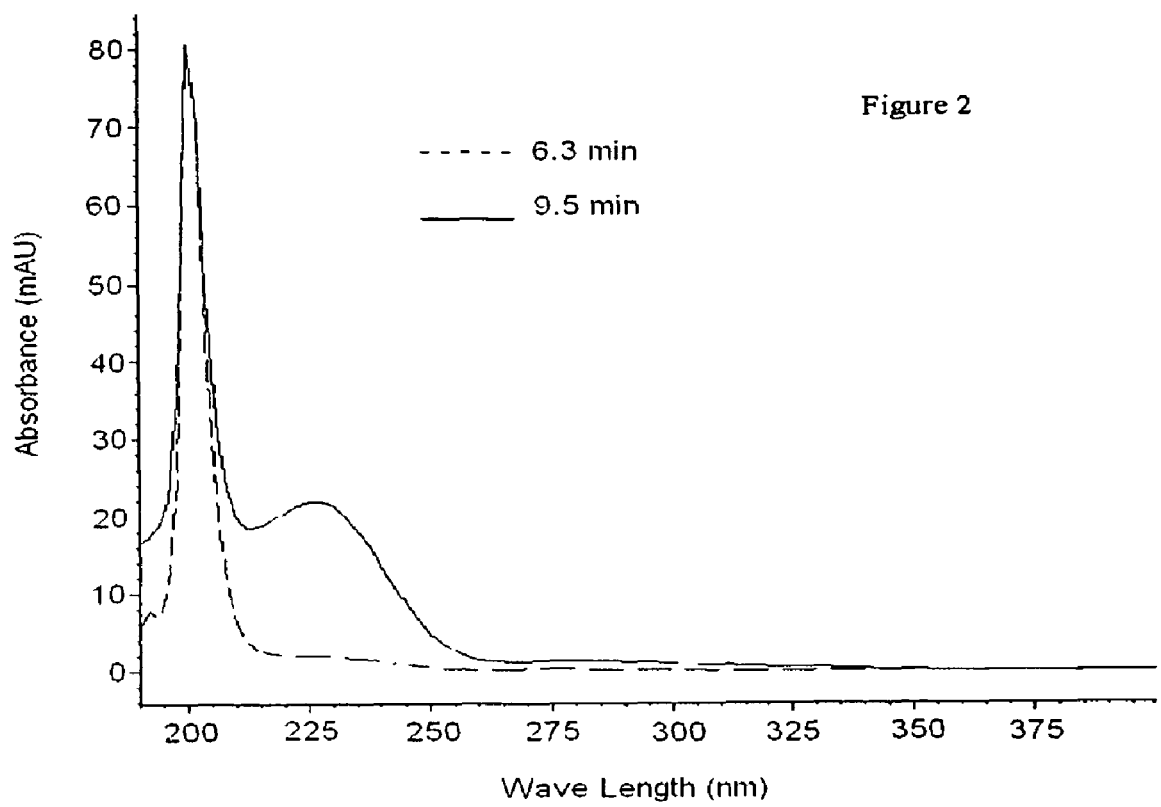
FIG. 2 shows a UV absorbance spectrum of the large PQ1 molecules according to comparative example 1 (without acid added) with peaks at retention times 6.3 minutes and 9.5 minutes.

As can be seen in FIG. 2, the crude PQ1 product synthesized as described in the U.S. Pat. No. 4,027,020 patent without adding acid shows absorbance at 228 nm. The absorbance peak shifts to a longer retention time with increase of reaction time from 8.4 min at 2 hours (see FIG. 1a) to 9 minutes at 10 hours (see FIG. 1c). FIG. 2 further shows that the spectrum of the large PQ1 molecules at retention time of 6.3 minutes has no absorbance at 228 nm and that the spectrum at 9.5 minutes possess a strong absorbance at 228 nm. Clearly, there are two or more types of different polymeric quaternary amines generated in the product mixture. The large polymers are close to PQ1 and the small polymers correspond to the degraded PQ1.

In the present embodiments, any acid can be used in the synthetic method. In preferred embodiments, the acid used does not contain a strong nucleophilic group. Preferred acids include HCl, $H_2SO_4$, and $H_3PO_4$ but the present embodiments are not limited to these acids. Additional suitable acids include acetic acid, succinic acid, and citric acid, among others.

COMPARATIVE EXAMPLE 2

FIG. 5 shows the GPC chromatograms for the products of the reaction as described above in Comparative Example 1 except with a specific reaction admixture of 1 mole of 1,4-bis-dimethylamino-2-butene, 1.2 moles of TEA, and 1.2 moles of 1,4-dichlo-butene at 60° C. for 18 hours. No acid was added to the reaction admixture.

The severe degradation during synthesis process is shown with strong absorption at 228 nm. The long retention time also indicates that PQ1 was degraded into smaller molecular size. Another indication of PQ1 degradation in the absence of acid is the increase of peak area at the retention time of 10.5 minutes over reaction time from FIGS. 1 and 5. This peak corresponds to non-polymeric small molecules with similar absorbance spectrum maximum at 225 nm as that of 228 nm for one of the degraded PQ1 molecules. It is likely that all PQ1 will eventually be degraded in to the small molecules during reaction or storage if the time is long enough.

COMPARATIVE EXAMPLE 3

In order to prevent the side end-capping reaction and increase the main end-capping reaction rate, the amount of TEA in the admixture of the reactants was increased. Table 2 shows the proton NMR spectrum data for PQ1 synthesized at 65° C. with admixture of 1 mole of 1,4-bis-dimethylamino-2-butene, 0.9 moles of TEA, and 1.15 moles of 1,4-dichlobutene (the molar ratio of 1,4-bis-dimethylamino-2-butene with TEA is 1.11:1 instead of 5:1 as in Example 1 above). The far right column of Table 2 lists the end-capping percentage over the reaction time. It can be seen that even at the presence of large excess amount of TEA, the reaction is still not complete until a time of 4 hours. See FIGS. 1 and 2.

TABLE 2

| Reaction Time | Peak area at 6.5 ppm Chemical shift | Peak area at 3.7 ppm Chemical shift | End-capping efficiency |
|---|---|---|---|
| 2 hours | 1.000 | 0.108 | 94.7% |
| 4 hours | 1.000 | 0.114 | 100% |
| 6 hours | 1.000 | 0.114 | 100% |

EXAMPLE 1

10.14 grams (71.3 mmoles) of 1,4-bis-dimethylamino-2-butene, 6.4 grams (42.8 mmoles) of TEA, 4.92 ml of 6N HCl (29.5 mmoles), 18.8 grams of water and a stir bar were combined in a 100 ml three-mouth flask. The flask was submerged into an ice water bath. 9.8 grams of (78.4 mmoles) of 1,4-dichloro-2-butene were slowly added drop-wise into the flask under constant stirring. The ice-bath was removed after the 1,4-dichloro-2-butene was completely added and the flask was submerged in a warm-water bath (25-40° C.) for 20 minutes. The water bath was heated until the temperature inside the flask reached 70° C. The reaction was stopped after 21 hours by removing the flask from the water bath. Variations can be made to the procedure by those skilled in the art for larger scale production to release the heat generated at the initial stage of the reaction before raising the temperature to above 60° C.

Figure 3B:
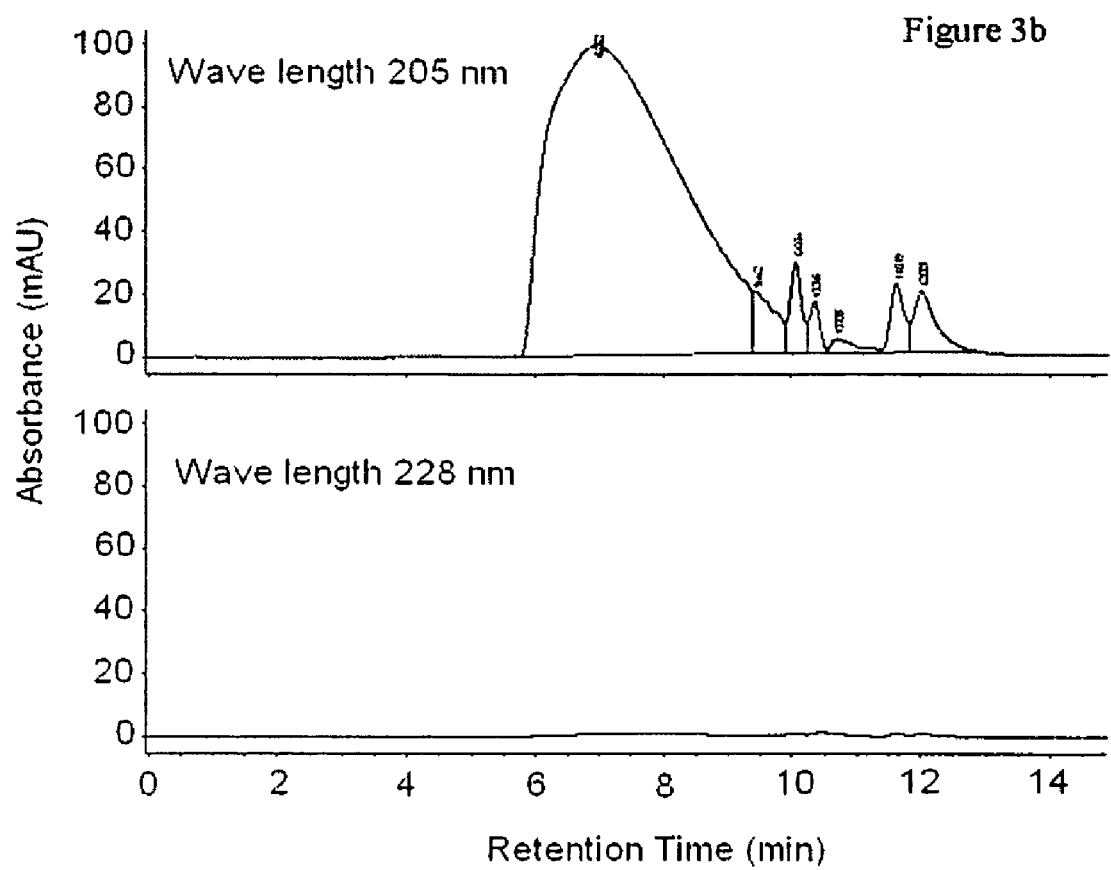
FIG. 3 shows the GPC chromatograms for the products of example 1 having acid added.
Figure 4:
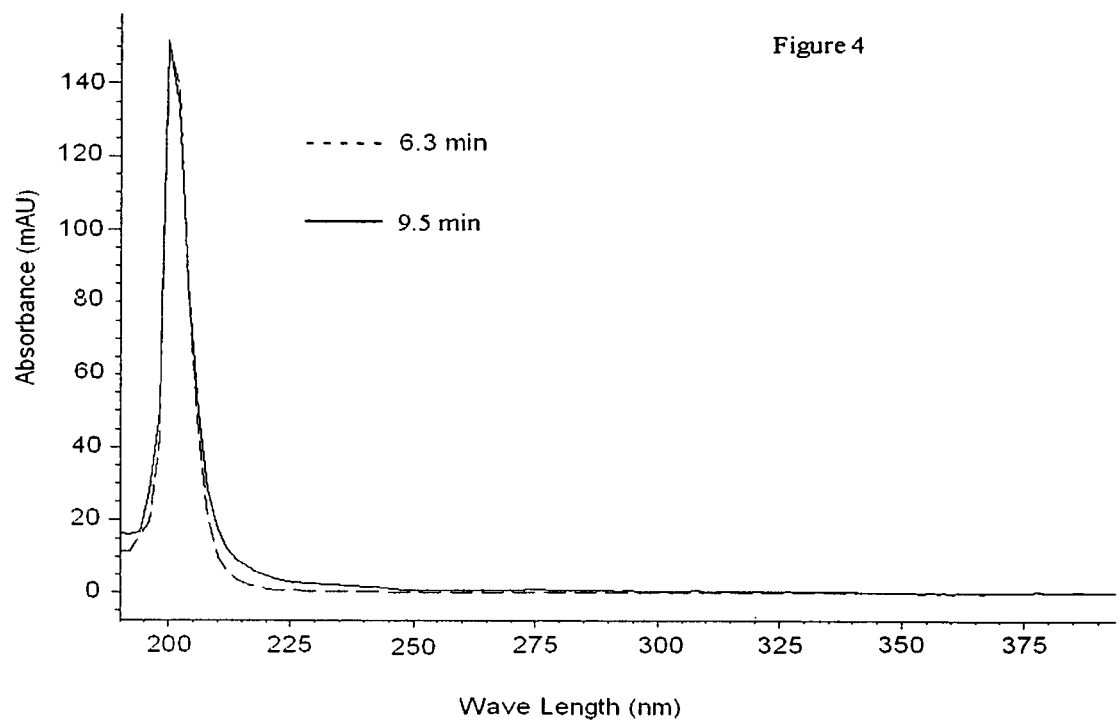
FIG. 4 shows a UV absorbance spectrum of the synthesized crude product in example 1 at 6 hours reaction time, with peaks at retention times 6.3 and 9.5 minutes.

FIGS. 3a, 3b and 3c are the GPC chromatograms for the above admixtures with HCl added. The peak at 205 nm in each chromatogram shows the presence of PQ1, while the lack of peak at 228 nm indicates the absence of degradation products. FIG. 4 is the spectra of the synthesized crude product at 6 hours reaction time at 6.3 and 9.5 minutes retention time, respectively. It can be seen that there is no absorbance at 228 nm in the whole 10 hours reaction period when the acid is added to the reaction mixture, indicating that no degraded PQ1 has been formed. FIG. 4 further confirms that there is no absorbance peak at 228 nm at the whole retention time range of 6-10 minutes. This result indicates that the addition of the acid effectively prevented the formation of degraded PQ1.

TABLE 3

Summary of Peak Retention Time for the Products Synthesized with and without Acid

| Reaction Time | Peak retention time without acid | | Peak retention time with acid | |
|---|---|---|---|---|
| | 205 nm | 228 nm | 205 nm | 228 nm |
| 2 hours | 6.7 | 8.4 | 6.9 | no peak |
| 6 hours | 7.3 | 8.9 | 6.9 | no peak |
| 10 hours | 7.6 | 9.0 | 6.9 | no peak |

The absorbance at 205 nm is mainly from the molecule back-bone structure. Table 3 further shows that the polymer molecular size distribution measured at 205 nm is stable in the system where the acid is added.

As one of ordinary skill in the art will appreciate, the above crude PQ1 products can be purified by removing the excess amount of TEA, the acid, 1,4-dichloro-2-butene and other small molecule byproduct/impurities which are shown up at the retention time of >10 minutes in FIGS. 1 and 3 using methanol and/or acetone as solvents.

EXAMPLE 2

Polyquaternium-1 Synthesis Procedure for Sample #2 in Table 4

10.14 grams (71.3 mmoles) of 1,4-bis-dimethylamino-2-butene, 6.4 grams (42.8 mmoles) of TEA, 4.92 ml of 6N HCl (29.5 mmoles), 18.8 grams of water and a stir bar were combined in a 100 ml three-mouth flask. The flask was then submerged into an ice water bath. 9.8 grams (78.4 mmoles) of 1,4-dichloro-2-butene were added (drop-wise) into the flask under constant stirring. The ice-bath was removed after all of the 1,4-dichloro-2-butene was completely added and the flask was submerged into a warm-water bath (25-40° C.) for 20 minutes. The water bath was heated until the temperature in the flask reached 70° C. The reaction was stopped after 21 hours by removing the flask from the water bath.

Table 4 lists PQ1 synthesized with addition of acid to the reaction mixture. Each sample was prepared as described above for Sample #2 except with different molar ratios of reactants. No absorbance was observed at 228 nm, i.e., no degradation of PQ1 occurred for any of the samples. The molecular weight was measured by the proton NMR method.

TABLE 4

| Sample # | Molar ratio | | Reaction Time | Reaction Temperature | PQ1 Molecular weight |
|---|---|---|---|---|---|
| | DA*/TEA | DA/DCB*/HCl | | | |
| 1 | 0.83 | 1/1.2/0.83 | 5 hours | 70° C. | 6.94k |
| 2 | 1.67 | 1/1.1/0.41 | 21 hours | 70° C. | 11.4k |
| 3 | 1.25 | 1/1.1/0.55 | 8 hours | 75° C. | 9.3k |
| 4 | 0.83 | 1/1.2/0.83 | 8 hours | 60° C. | 7.7k |
| 5 | 1.11 | 1/1.15/0.62 | 6 hours | 60° C. | 10k |
| 6 | 5.0 | 1/1.1/1 | 18 hours | 75° C. | 26k |

*DA = 1,4-bis-dimethylamino-2-butene, DCB = 1,4-dichloro-butene

As described in U.S. Pat. No. 4,027,020, PQ1 synthesis without the addition of acid to the reaction mixture is not effective outside the range of DA/TEA molar ratio of 2:1-30:1. Table 4 above shows that the methods of the present embodiments are effective with a much larger ranger of DA/TEA molar ratios. In some embodiments, PQ1 can be effectively formed at DA/TEA molar ratio <2:1. In fact, the molecular size of PQ1 is related to the ratio of DA/TEA: the higher the ratio, the higher the PQ1 molecular weight.

The preferred molar ratio of the total amines (DA+TEA) to acid is from about 10:1 to about 1:2 and most preferably from about 5:1 to about 1:1. The preferred DA/TEA ratio is from about 0.3:1 to about 30:1 and most preferably from 0.8:1 to about 5:1.

The molecular weights are deduced from the proton NMR spectrum of the product according to the equation: mw=133.5 (6 u/v−1)+290, where u is the peak area at the chemical shift of 6.5 ppm which is from the vinyl protons in the repeating units, and v is peak area at the chemical shift of 3.7 ppm which is from the allylic protons adjacent to nitrogen in the ending groups of the PQ1 molecules.

EXAMPLE 3

An experiment was done to test the anti-bacterial effect of PQ1 synthesized in the presence of acid in comparison to PQ1 molecules synthesized without the presence of acid. Several contact lens multi-purpose solutions were formulated by dissolving the ingredients in Table 5 in deionized water. Antimicrobial activity was tested by methods known in the art against the FDA contact lens disinfection panel. Log reductions at 6 hours solution contact are reported at the bottom of Table 5.

TABLE 5

|  | % w/w PQ1 synthesized with acid added (sample# 5 in Table 4) | | | % w/w PQ1 synthesized without acid* | | |
| --- | --- | --- | --- | --- | --- | --- |
| PQ1 | 0.000075 | 0.0001 | 0.00015 | 0.000075 | 0.0001 | 0.00015 |
| Hydroxypropylmethylcellulose (HPMC) | 0.20 | 0.20 | 0.20 | 0.20 | 0.20 | 0.20 |
| Sodium Chloride | 0.59 | 0.59 | 0.59 | 0.59 | 0.59 | 0.59 |
| Potassium Chloride | 0.14 | 0.14 | 0.14 | 0.14 | 0.14 | 0.14 |
| Tris HCl | 0.055 | 0.055 | 0.055 | 0.055 | 0.055 | 0.055 |
| Tris (base) | 0.021 | 0.021 | 0.021 | 0.021 | 0.021 | 0.021 |
| Taurine | 0.05 | 0.05 | 0.05 | 0.05 | 0.05 | 0.05 |
| Poloxamer 237 | 0.05 | 0.05 | 0.05 | 0.05 | 0.05 | 0.05 |
| Edetate Disodium | 0.01 | 0.01 | 0.01 | 0.01 | 0.01 | 0.01 |
| Propylene Glycol | 0.50 | 0.50 | 0.50 | 0.50 | 0.50 | 0.50 |
| Purified Water | 98.38 | 98.38 | 98.38 | 98.38 | 98.38 | 98.38 |
| Log drop at 6 hours | | | | | | |
| S. marcescens 13880 | 2.12 | 2.18 | 2.18 | 0.01 | 0.14 | 0.37 |
| C. albicans 10231 | 0.36 | 0.54 | 0.45 | 0.21 | 0.21 | 0.17 |
| P. aeruginosa 9027 | >5.00 | >5.00 | >5.00 | | | |
| S. aureus 6538 | 2.89 | 2.99 | 3.32 | | | |
| F. solani 36031 | 2.65 | 2.90 | 3.40 | | | |

*Synthesized according to the conditions described in Comparative Example 2 except the reaction time is 40 hours.

As can be seen in Table 5, above, the antimicrobial activity is reduced considerably when PQ1 is generated without the presence of acid; that is, when PQ1 is degraded. Killing 99.999% of bacteria in a sample may be express as a 5 log reduction. Killing 99.999% of microbes means that 0.001% of the microbes survived. We started with 100% microbes and Log (100%)=0. If we have 0.001% surviving microbes, then Log (0.001%)=−5. The reduction or killing of the microbes at log scale is 0−(−5)=5. So, in the disinfecting community, 99.999% killing is called a 5 log reduction.

EXAMPLE 4

5.86 grams (41.2 mmoles) of 1,4-bis-dimethylamino-2-butene, 1.24 grams (8.3 mmoles) of TEA, 1 ml of 6N HCl (6 mmoles), 10 grams of water and a stir bar were combined in a 50 ml three-mouth flask. 5.6 grams of (44.8 mmoles) of 1,4-dichloro-2-butene were slowly added drop-wise into the flask under constant stirring. After the 1,4-dichloro-2-butene was completely added the flask was heated until the temperature inside the flask reached 70° C. One hour later, another mixture of 1.24 grams of TEA and 1 ml of 6N HCl was added to the flask. The reaction was stopped after 6 hours by removing the flask from the water bath. The molecular weight of PQ1 measured by 1H NMR is about 34,000 Dalton, which is much higher than that seen in Comparative Example 4.

One of ordinary skill in the art will understand how to vary this procedure, as well as all others disclosed in this application, to scale it up for larger production. For example, variations can be made to the procedure for larger scale the production to release the heat generated at the initial stage of the reaction before raising the temperature to above 60° C.

COMPARATIVE EXAMPLE 4

PQ1 was also synthesized with the method disclosed in U.S. patent application Ser. No. 11/609,422, with the same amount 1,4-bis-dimethylamino-2-butene, total TEA, total 6N HCl, 1,4-dichloro-2-butene and water, and with the same reaction temperature and time, as was shown in Example 4, except the second part of TEA/HCl mixture was combined with the first part of TEA/HCl mixture. That is, 41.2 mmoles of 1,4-bis-dimethylamino-2-butene, 16.6 mmoles of TEA, 12 mmoles of HCl and 10 grams of water were combined in a 50 ml three-mouth flask. 44.8 mmoles of 1,4-dichloro-2-butene were slowly added drop-wise into the flask under constant stirring. After the 1,4-dichloro-2-butene was completely added the flask was heated until the temperature inside the flask reached 70° C. The reaction was stopped after 6 hours by removing the flask from the water bath. The molecular weight of PQ1 measured by 1H NMR is about 14,000 Dalton.

High Mw PQ1 as an Antimicrobial Agent in MPS

High molecular weight PQ1 has much higher antimicrobial activities than low molecular weight PQ1 at the same concentration level. Therefore, the eye irritation can be reduced or avoided by using high molecular weight PQ1 as a preservative/disinfecting agent for MPS or ophthalmic compositions.

The examples below show that the activity enhancement for Sm, Fs and Ap is very significant when the PQ1 average molecular weight is increased from 6-7 k to about 22-34 k.

Compositions according to the present invention may include one or more of the following components in addition to the high molecular weight PQ1: additional antimicrobial component(s), surfactant(s), viscosity or thickening agent(s), tonicity agent(s), chelating agent(s) and buffer(s). The additional component or components may be selected from materials which are known to be useful in contact lens care compositions and are included in amounts effective to provide the desired effect or benefit. When an additional component is included, it is generally compatible under typical use and storage conditions with the other components of the composition. For instance, the aforesaid additional component or components are substantially stable in the presence of the antimicrobial and buffer components described herein.

The presently useful additional antimicrobial components include chemicals which derive their antimicrobial activity through a chemical or physiochemical interaction with microbes or microorganisms, such as those contaminating a contact lens. The additional antimicrobial component may be any suitable, preferably ophthalmically acceptable, material effective to disinfect a contact lens contacted with the present solutions or alternatively adequately preserve a solution such as a contact lens rewetting solution.

By way of example, and not of limitation, the additional antimicrobial component may be a monomeric quaternary ammonium or biguanide compound such as chlorhexidine digluconate, chlorhexidine diacetate, benzethonium chloride, myristamidopropyldimethylamine or poly [oxyethylene (dimethyliminio) ethylene-(dimethyliminio) ethylene dichloride] (sold under the trademark WSCP by Buckman Laboratories, Inc.). The additional antimicrobial component may also include, but may not be limited to, other quaternary ammonium salts used in ophthalmic applications, benzalkonium halides, and biguanides, such as salts of alexidine, alexidine-free base, salts of chlorhexidine, hexamethylene biguanides and their polymers, and salts thereof, antimicrobial polypeptides, chlorine dioxide precursors, and the like and mixtures thereof. Generally, the hexamethylene biguanide polymers (PHMB), also referred to as polyaminopropyl biguanide (PAPB), have molecular weights of up to about 100, 000. Such compounds are known and are disclosed in Ogunbiyi et al, U.S. Pat. No. 4,759,595, the disclosure of which is hereby incorporated in its entirety by reference herein.

Generally, the antimicrobial component(s) are present in the liquid aqueous medium at an ophthalmically acceptable or safe concentration such that the user can remove the disinfected lens from the liquid aqueous medium and thereafter directly place the lens in the eye for safe and comfortable wear. Alternatively, the antimicrobial component is present in the liquid aqueous medium at an ophthalmically acceptable or safe concentration and sufficient for maintaining preservative effectiveness. The additional antimicrobial components useful in the present invention preferably are present in the liquid aqueous medium in concentrations in the range of about 0.00001% to about 0.01% (w/v), and more preferably in concentrations in the range of about 0.00005% to about 0.001% (w/v) and most preferably in concentrations in the range of about 0.0001% to about 0.0005% (w/v). Alternatively, the additional antimicrobial component may be present in an amount in the range of from about 0.00001% (w/v) to about 0.0003% (w/v) or about 0.0005% (w/v) or less than 0.005% (w/v).

In one embodiment of the present invention, the additional antimicrobial component is non-oxidative. It has been found that reduced amounts of non-oxidative antimicrobial components, for example, in a range of about 0.1 ppm to about 3 ppm or less than 5 ppm (w/v), in the present compositions are effective in disinfecting contact lenses and reduce the risk of such antimicrobial components causing ocular discomfort and/or irritation. Such reduced concentration of antimicrobial component is very useful when the antimicrobial component employed is selected from biguanides, biguanide polymers, salts thereof and mixtures thereof.

The surfactant component generally is present in an amount effective in cleaning, that is to at least facilitate removing, and preferably effective to remove, debris or deposit material from, a contact lens contacted with the surfactant containing solution. Classes of suitable surfactants include poloxamers and poloxamines. Exemplary surfactant components include, but are not limited to, Tetronic 1307, Tetronic 1107, Tetronic 1304, Tetronic 904, Pluronic F87, Pluronic F127, and mixtures thereof. The amount of surfactant component present, if any, varies over a wide range depending on a number of factors, for example, the concentration of the antimicrobial(s) being used, the specific surfactant or surfactants being used, the other components in the composition and the like. Often the amount of surfactant is in the range of about 0.0003% or about 0.002% to about 0.1% or about 0.5% or about 1.0% (w/v).

By way of further example, and not of limitation, suitable non-ionic surfactants may include block copolymers, tridecyl alcohol ethoxylates, stearyl alcohol ethoxylates, polyethylene glycol esters, octylphenol ethoxylates, nonylphenol ethoxylates, national formulary block copolymers, lauryl alcohol ethoxylates, glycerol esters, ethylene/propylene oxide block copolymers, ethoxylated sorbitan fatty acid esters, decyl alcohol ethoxylates, amine oxides, amine based block copolymers, alcohol ethoxylates, and alcohol alkoxylates.

Any suitable, preferably ophthalmically acceptable viscosity inducing or thickening agent may be included in the present compositions. The viscosity inducing components employed in the present solutions preferably are effective at low or reduced concentrations, compatible with the other components of the present solutions, and anionic or non-ionic. Such viscosity inducing components are effective to enhance and/or prolong the cleaning and wetting activity of the surfactant component and/or condition the lens surface rendering it more hydrophilic (less lipophilic) and/or to act as a demulcent on the eye. Increasing the solution viscosity provides a film on the lens which may facilitate comfortable wearing of the treated contact lens. The viscosity inducing component may also act to cushion the impact on the eye surface during insertion and serves also to alleviate eye irritation. Without wishing to limit the invention to any particular theory of operation, it is believed that the presence of a viscosity inducing component at least assists in providing the lens wearer/user comfort and acceptability benefits of the present invention, which promote regular and consistent contact lens care and ultimately lead to or facilitate better ocular health. The present combinations of components, for example, including such viscosity inducing components, are effective in providing the degree of lens wearer/user comfort and acceptability benefits described herein.

Suitable viscosity inducing components include, but are not limited to, water soluble natural gums, cellulose-derived polymers and the like. Useful natural gums include guar gum, gum tragacanth and the like. Useful cellulose-derived viscosity inducing components include cellulose-derived polymers, such as hydroxypropyl cellulose, hydroxypropylmethyl cellulose, carboxymethyl cellulose, methyl cellulose, hydroxyethyl cellulose and the like. More preferably, the viscosity inducing agent is selected from hyaluronic acid, cellulose derivatives (polymers) and mixtures thereof. A very useful viscosity inducing component is hydroxypropylmethyl cellulose (HPMC).

The viscosity inducing component is used in an amount effective to increase the viscosity of the solution, preferably to a viscosity in the range of about 1.5 to about 30 cps at 25.degree. C., as determined by USP test method No. 911 (USP 23, 1995). To achieve this range of viscosity increase, an amount of viscosity inducing component of about 0.01% to about 5% (w/v) preferably is employed, with amounts of about 0.05% to about 0.5% being more preferred.

The liquid aqueous medium may also include an effective amount of a tonicity component to provide the liquid medium with the desired tonicity. Such tonicity components may be present in the liquid aqueous medium and/or may be introduced into the liquid aqueous medium. Among the suitable tonicity adjusting components that may be employed are those conventionally used in contact lens care products, such as various inorganic salts. Sodium chloride and/or potassium chloride and the like are very useful tonicity components. The amount of tonicity component included is effective to provide the desired degree of tonicity to the solution. Such amount may, for example, be in the range of about 0.1% to about 1.5% (w/v). If a combination of sodium chloride and potassium chloride is employed, it is preferred that the weight ratio of sodium chloride to potassium chloride be in the range of about 2.5 to about 6 or about 8.

The present compositions preferably include a chelating or sequestering component in an amount effective to enhance the effectiveness of the antimicrobial component and/or to complex with metal ions to provide more effective cleaning of the contact lens. A wide range of organic acids, amines or compounds which include an acid group and an amine function are capable of acing as chelating components in the present compositions. For example, nitrilotriacetic acid, diethylenetriaminepentacetic acid, hydroxyethylethylene-diaminetriacetic acid, 1,2-diaminocyclohexane tetraacetic acid, hydroxyethylaminodiacetic acid, ethylenediamine-tetraacetic acid and its salts, polyphosphates, citric acid and its salts, tartaric acid and its salts, and the like and mixtures thereof, are useful as chelating components. Ethylenediaminetetraacetic acid (EDTA) and its alkali metal salts, are preferred, with disodium salt of EDTA, also known as disodium edetate, being particularly preferred. The chelating component preferably is present in an effective amount, for example, in a range of about 0.01% and about 1% (w/v) of the solution.

Any suitable, preferably ophthalmically acceptable buffer component may be included in the present composition. Phosphate, organic amine (e.g., tromethamine) or boric acid buffers are preferred, in an amount effective in maintaining the pH of the composition within a physiologically acceptable range.

The buffer component is present in an amount effective to maintain the pH of the composition or solution in the desired range, for example, in a physiologically acceptable range of about 6 to about 7.5 or about 8.5. In particular, the solution has a pH in the range of about 7 to about 8. The buffer component may include one or more phosphate or tromethamine (TRIS, 2-amino-2-hydroxymethyl-1,3-propanediol) or boric buffers, for example, combinations of monobasic phosphates, dibasic phosphates and the like, or tromethamine and tromethamine hydrochloride. Particularly useful phosphate buffers are those selected from phosphate salts of alkali and/or alkaline earth metals. Examples of suitable phosphate buffers include one or more of sodium phosphate dibasic ($Na_2HPO_4$) sodium phosphate monobasic ($NaH_2PO_4$) and potassium phosphate monobasic ($KH_2PO_4$). The buffer may be a boric acid/sodium hydroxide buffer or a boric acid/sodium borate buffer. The buffer component may also include an amino acid such as taurine. The present buffer components frequently are used in amounts in a range of about 0.01% or about 0.02% to about 0.5% or about 1% (w/v).

Various combinations of two or more of the above noted components may be used in providing at least one of the benefits described herein. Therefore, each and every such combination is included within the scope of the present invention.

In one embodiment, the present compositions comprise: a liquid aqueous medium, high molecular weight polyquaternium-1; a non-ionic surfactant component in an amount effective in cleaning a contact lens contacted with the composition; a buffer component in an amount effective in maintaining the pH of the composition within a physiologically acceptable range; an effective amount of a viscosity inducing component; and an effective amount of a tonicity component. The present compositions may also include an effective amount of a chelating or sequestering component. Each of the components, in the concentration employed, included in the solutions and the formulated solutions of the present invention generally are ophthalmically acceptable. In addition, each of the components in the concentration employed included in the present solutions usually is soluble in the liquid aqueous medium. The solution may also optionally include an additional antimicrobial component in an amount effective to, in association with the remainder of the solution, disinfect a contact lens contacted with the composition.

A solution or component thereof is "ophthalmically acceptable" when it is compatible with ocular tissue, that is, it does not cause significant or undue detrimental effects when brought into contact with ocular tissue. Preferably, each component of the present compositions is also compatible with the other components of the present compositions. The present compositions are more preferably substantially ophthalmically optimized. An ophthalmically optimized composition is one which, within the constraints of component chemistry, minimizes ocular response, or conversely delivers ophthalmic benefit to the lens wearing eye.

When a contact lens is desired to be disinfected by the present compositions, a total amount of antimicrobial component(s) effective to disinfect the lens is used. Generally, such an effective amount of the antimicrobial component reduces the microbial burden or load on the contact lens by one log order in three hours. More preferably, an effective amount of the disinfectant reduces the microbial load by one log order in one hour.

The liquid aqueous medium used is selected to have no substantial deleterious effect on the lens being treated, or on the wearer of the treated lens. The liquid medium is constituted to permit, and even facilitate, the lens treatment or treatments by the present compositions. The liquid aqueous medium advantageously has an osmolality in the range of at least about 175 mOsmol/kg or about 200 mOsmol/kg to about 300 or about 350 mOsmol/kg. The liquid aqueous medium more preferably is substantially isotonic or hypotonic (for example, slightly hypotonic) and/or is ophthalmically acceptable.

Methods for treating a contact lens using the herein described compositions are included within the scope of the invention. Such methods comprise contacting a contact lens with such a composition at conditions effective to provide the desired treatment to the contact lens. Such methods may also include a rubbing step (from about 2 seconds to about 4 or 6 or more seconds per side) and/or a soaking step. The contacting temperature is preferred to be in the range of about 0° C. to about 100° C., and more preferably in the range of about 10° C. to about 60° C., and still more preferably in the range of about 15° C. to about 30° C. Contacting at or about ambient temperature is very convenient and useful. The contacting preferably occurs at or about atmospheric pressure. The contacting preferably occurs for a time in the range of about 5 minutes or about 1 hour to about 8 or about 12 hours or more.

The contact lens can be contacted with the liquid aqueous medium by immersing the lens in the medium. During at least a portion of the contacting, the liquid medium containing the contact lens optionally may be agitated, for example, by shaking the container containing the liquid aqueous medium and contact lens, to at least facilitate removal of deposit material from the lens. After such contacting step, the contact lens optionally may be manually rubbed to remove further deposit material from the lens. The cleaning method optionally may also include rinsing the lens substantially free of the liquid aqueous medium prior to returning the lens to a wearer's eye. The rinsing step may be accomplished using the solution formulated according to the present invention.

The present will now be described with regards to some embodiments, though the skilled practitioner will realize that the novel disinfecting compounds according to the present invention may be used in a wider variety of applications.

Table 6 shows antimicrobial activities for two 0.75 ppm PQ1 solutions with average molecular weight of 30,000 and 7,000 Dalton, respectively. The tests were conducted in test tube with 0.3% organic soil added and without contact lens. The increase in activity with increase of molecular weight is listed in the right column. As may be seen, the higher MW PQ1 had much stronger activity against S. marcescens, F. solani and C. albicans than the 6K PQ1.

TABLE 6

| Ingredients | #1 % w/w | #2 % w/w | Log drop increase with PQ1 MW increase |
|---|---|---|---|
| 30K PQ1 | 0.000075 | | |
| 7 k PQ1 | | 0.000075 | |
| Boric acid | 0.60 | 0.60 | |
| Sodium Borate-10H2O | 0.18 | 0.18 | |
| NaCl | 0.40 | 0.40 | |
| EDTA | 0.05 | 0.05 | |
| Tetronic 904 | 0.10 | 0.10 | |
| Pluronic F87 | 0.05 | 0.05 | |
| Log drops @ 6 hours | | | |
| S. marcescens 13880 | 2.98 | 1.58 | 1.4 |
| C. albicans 10231 | 3.43 | 2.77 | 0.66 |
| F. solani 36031 | 4.17 | 2.45 | 1.72 |

Table 7 shows antimicrobial activities for two 1.5 ppm PQ1 solutions with average molecular weight of 30,000 and 7,000 Dalton, respectively. The tests were also conducted in test tube with 0.3% organic soil added and without contact lens. The increase in activity with increase of molecular weight is listed in the right column. As may be seen, the higher MW PQ1 had much stronger activity against S. marcescens, C. albicans and F. solani than the 6K PQ1.

TABLE 7

| Ingredients | #3 % w/w | #4 % w/w | Log drop increase with PQ1 MW increase |
|---|---|---|---|
| 30K PQ1 | 0.00015 | | |
| 7 k PQ1 | | 0.00015 | |
| Boric acid | 0.60 | 0.60 | |
| Sodium Borate-10H2O | 0.18 | 0.18 | |
| NaCl | 0.40 | 0.40 | |
| EDTA | 0.05 | 0.05 | |
| Tetronic 904 | 0.10 | 0.10 | |
| Pluronic F87 | 0.05 | 0.05 | |
| Log drops @ 6 hours | | | |
| S. marcescens 13880 | 3.19 | 2.56 | 0.63 |
| C. albicans 10231 | 3.46 | 3.35 | 0.11 |
| F. solani 36031 | 4.17 | 3.87 | 0.3 |

Table 8 shows antimicrobial activities for two 7 ppm PQ1 solutions with average molecular weight of 34,000 and 6,000 Dalton, respectively. The tests were conducted in lens case with a Acuvue2 contact lens and 0.003% organic soil added. The contact lenses were added while the microorganisms were inoculated to the solution. The increase in activity with increase of molecular weight is listed in the right column. As may be seen, the higher MW PQ1 had much stronger activity against S. marcescens, S. Aureus and F. solani than the 6KPQ1.

TABLE 8

| Ingredients | % w/w | % w/w | Log drop increase with PQ1 MW increase |
|---|---|---|---|
| 34k PQ1 | 0.0007 | | |
| 6k PQ1 | | 0.0007 | |
| Trisodium citrate | 0.65 | 0.65 | |
| Boric acid | 0.60 | 0.60 | |
| Sodium borate, 10 hydrate | 0.125 | 0.125 | |
| NaCl | 0.30 | 0.30 | |
| EDTA | 0.05 | 0.05 | |
| Tetronic 904 | 0.10 | 0.10 | |
| Pluronic F87 | 0.05 | 0.05 | |
| Log drops @ 6 hours | | | |
| S. marcescens | 2.14 | 0.80 | 1.34 |
| S. aureus | 2.97 | 2.59 | 0.38 |
| F. solani | 3.63 | 1.93 | 1.70 |

Table 9 shows antimicrobial activities for two 10 ppm PQ1 solutions with average molecular weight of 34,000 and 6,000 Dalton, respectively. The tests were conducted in lens case with a Acuvue2 contact lens and 0.003% organic soil added. The contact lenses were added while the microorganisms were inoculated to the solution. The increase in activity with increase of molecular weight is listed in the right column. As may be seen, the higher MW PQ1 had much stronger activity against S. marcescens, S. Aureus and F. solani than the 6KPQ1.

TABLE 9

| Ingredients | % w/w | % w/w | Log drop increase with PQ1 MW Increase |
|---|---|---|---|
| 34k PQ1 | 0.001 | | |
| 6k PQ1 | | 0.001 | |
| Trisodium citrate | 0.65 | 0.65 | |
| Boric acid | 0.60 | 0.60 | |
| Sodium borate, 10 hydrate | 0.125 | 0.125 | |
| NaCl | 0.30 | 0.30 | |
| EDTA | 0.05 | 0.05 | |
| Tetronic 904 | 0.10 | 0.10 | |
| Pluronic F87 | 0.05 | 0.05 | |
| Log drops @ 6 hours | | | |
| S. marcescens | 2.07 | 0.88 | 1.19 |
| S. aureus | 3.12 | 2.78 | 0.34 |
| F. solani | 4.18 | 1.95 | 2.23 |

Table 10 shows anti-Acanthamoeba activities for 7 and 10 ppm PQ1 solutions with average molecular weight of 34,000 and 6,000 Dalton, respectively. The tests were conducted in test tube with 0.3% organic soil added. As may be seen, for both concentrations tested, the anti-Acanthamoeba activity is significantly higher with the higher molecular weight PQ1.

TABLE 10

| Ingredients | % w/w | % w/w | % w/w | % w/w |
|---|---|---|---|---|
| 34k PQ1 | 0.0007 | 0.0010 | | |
| 6k PQ1 | | | 0.0007 | 0.0010 |
| Trisodium citrate | 0.65 | 0.65 | 0.65 | 0.65 |
| Boric acid | 0.60 | 0.60 | 0.60 | 0.60 |
| Sodium borate, 10 hydrate | 0.125 | 0.125 | 0.125 | 0.125 |
| NaCl | 0.30 | 0.30 | 0.30 | 0.30 |
| EDTA | 0.05 | 0.05 | 0.05 | 0.05 |
| Tetronic 904 | 0.10 | 0.10 | 0.10 | 0.10 |

TABLE 10-continued

| Ingredients | % w/w | % w/w | % w/w | % w/w |
|---|---|---|---|---|
| Pluronic F87 | 0.05 | 0.05 | 0.05 | 0.05 |
| Log drops @ 6 hours | | | | |
| A polyphage | 1.09 | 1.36 | 0.14 | 0.88 |

Table 11 shows antimicrobial activities for 7 ppm PQ1 solutions with average molecular weight of 28,300, 22,900 and 6,000 Dalton, respectively. The tests were conducted in lens case with Acuvue2 contact lenses and 0.003% organic soil added. The microorganisms were inoculated 40 hours after the contact lenses were added to the solution. As may be seen, the 28.3 k and 22.9 k PQ1 perform similarly. Further, both of the higher MW PQls have much stronger activity against S. macescens, F. aolani and Acanthemoeba than the 6 k PQ1.

TABLE 11

| Ingredients | % w/w | % w/w | % w/w |
|---|---|---|---|
| 28.3k PQ1 | 0.0007 | | |
| 22.9k PQ1 | | 0.0007 | |
| 6k PQ1 | | | 0.0007 |
| Trisodium citrate | 0.65 | 0.65 | 0.65 |
| Boric acid | 0.60 | 0.60 | 0.60 |
| Sodium borate, 10 hydrate | 0.125 | 0.125 | 0.125 |
| NaCl | 0.30 | 0.30 | 0.30 |
| EDTA | 0.05 | 0.05 | 0.05 |
| Tetronic 904 | 0.10 | 0.10 | 0.10 |
| Pluronic F87 | 0.05 | 0.05 | 0.05 |
| Log Drops @ 6 hours | | | |
| S. marcescens 13880 | 2.01 | 2.03 | 1.26 |
| S. aureus 6538 | 2.77 | 2.45 | 2.37 |
| F. solani 36031 | >4.52 | >4.52 | 2.22 |
| A. polyphaga 30461 | 1.67 | 1.49 | 0.75 |

Table 12 shows antimicrobial activities for 10 ppm PQ1 solutions with average molecular weight of 28,300, 22,900 and 6,000 Dalton, respectively. The tests were conducted in lens case with Acuvue2 contact lenses and 0.003% organic soil added. The microorganisms were inoculated 40 hours after the contact lenses were added to the solution. As may be seen, the 28.3 k and 22.9 k PQ1 clearly outperform the 6 k PQ1. Further, both of the higher MW PQ1s have much stronger activity against S. macescens, F. solani and Acanthemoeba than 6 k PQ1.

TABLE 12

| Ingredients | % w/w | % w/w | % w/w |
|---|---|---|---|
| 28.3k PQ1 | 0.001 | | |
| 22.9k PQ1 | | 0.001 | |
| 6k PQ1 | | | 0.001 |
| Trisodium citrate | 0.65 | 0.65 | 0.65 |
| Boric acid | 0.60 | 0.60 | 0.60 |
| Sodium borate, 10 hydrate | 0.125 | 0.125 | 0.125 |
| NaCl | 0.30 | 0.30 | 0.30 |
| EDTA | 0.05 | 0.05 | 0.05 |
| Tetronic 904 | 0.10 | 0.10 | 0.10 |
| Pluronic F87 | 0.05 | 0.05 | 0.05 |
| Log Drops @ 6 hours | | | |
| S. marcescens 13880 | 2.19 | 2.21 | 1.26 |
| S. aureus 6538 | 3.03 | 2.64 | 2.38 |
| F. solani 36031 | >4.52 | >4.52 | 2.81 |
| A. polyphaga 30461 | 1.73 | 1.77 | 0.81 |

As demonstrated above, higher molecular weight PQ1 has much higher antimicrobial activities than low molecular weight PQ1 at the same concentration level. This is especially true when a contact lens is present during disinfection. To reach the same disinfection efficacy as that of high molecular weight PQ1, the low molecular weight PQ1 solutions have to have significantly higher PQ1 concentrations. A higher PQ1 concentration generally results in more PQ1 lens uptake. This increase in lens uptake generally results in a greater PQ1 release in the eye, and increased eye irritation. Therefore, the eye irritation can to reduced or avoided by using high molecular weight PQ1 as a preservative/disinfecting agent for MPS or ophthalmic compositions. Table 13 shows two different ophthalmic formulations, both of which contain the same concentration of PQ-1.

TABLE 13

| | 1 % w/w | 2 % w/w |
|---|---|---|
| Alexidine | 0.00018 | |
| 7k PQ1 | | 0.00018 |
| 30k PQ1 | 0.00018 | |
| Boric Acid | 0.6 | 0.6 |
| Sodium Borate 10H20 | 0.17 | 0.17 |
| NaCl | 0.4 | 0.4 |
| EDTA | 0.05 | 0.05 |
| Tetronic 904 | 0.1 | 0.1 |
| Pluronic F87 | 0.05 | 0.05 |
| HA | 0.0025 | 0.0025 |
| cytotoxicity score | 2 | 3 |

A direct overlay method which has been adopted by the FDA for MPS registration was used to evaluate the cytotoxicity profile of the PQ1 formulations. In this method, previously-soaked contact lenses (in 100 ml of the solutions to simulate overnight soak) were directly overlayed on L929 cells. The cytotoxicity result was evaluated by scoring each culture under a microscope on a relative scale of 0-4. A score of 2 indicates that cell damage is limited to the area under the lens. A score of 3 indicates that the cell damage extends 0.5 to 1.0 cm beyond the lens. Therefore, this shows that the high molecular weight PQ1 solution has a lower cytotoxicity than the low molecular weight PQ1 solution.

One possible explanation of the lower cytotoxicity is that the large PQ1 molecules are more difficult to get into the hydrogel lens matrix material do to the limited pore size of the lens material itself. As noted above, the lower the lens uptake of PQ1, the less PQ1 will be released to the cells. The reduced amount of high molecular weight PQ1 loss from the solution to the lens is consistent with the observation above that high molecular weight PQ1 is more efficacious against microbes in the presence of contact lenses.

All of the solutions according to the present invention which are described herein will provide substantial efficacy against the various microbes which may be found on the lenses, but will not be irritating to the eye. Furthermore, the solutions according to the present invention demonstrate reduced staining when compared to some of the currently marketed multi-purpose solutions.

Solutions according to the present invention may be manufactured either in multi-dose or unit dose packaging. If the solution is in a multidose configuration, such solution may require the addition of a preservative or second antimicrobial.

The foregoing written specification is considered to be sufficient to enable one skilled in the art to practice the invention. The foregoing description details certain preferred embodiments of the invention and describes the best mode contemplated by the inventor. It will be appreciated, however, that no matter how detailed the foregoing may appear in text, the invention may be practiced in many ways and the invention should be construed in accordance with the appended claims and any equivalents thereof.

What is claimed is:

1. A multipurpose solution for contact lens care, comprising:
   an aqueous liquid medium; and
   from about 0.00001% to about 0.01% w/w of polyquaternium-1 having a number average molecular weight as determined by a proton NMR method of 22,000 or more.

2. The solution of claim 1, wherein said polyquaternium-1 has a molecular weight of at least 30,000.

3. A multipurpose solution for contact lens care, comprising:
   an aqueous liquid medium; and
   from about 0.00001% to about 0.01% w/w of polyquaternium-1 obtained by a process of:
   a) mixing 1,4-bis-dimethylamino-2-butene, water, a first portion of triethanolamine and a first portion of acid;
   b) adding a 1,4-dichloro-2-butene and heating the reaction mixture;
   c) adding a second portion of triethanolamine and a second portion of acid, and
   d) isolating Polyquaternium-1 having a number average molecular weight as determined by a proton NMR method of 22,000 or more, at a yield of at least about 50%.

4. The solution of claim 3, wherein polyquaternium-1 has a molecular weight of at least 30,000.

5. The solution of claim 3, wherein the acid is selected from the group consisting of HCl, $H_2SO_4$ and $H_3PO_4$.

6. The solution of claim 3, wherein the acid is HCl.

7. The solution of claim 3, wherein the 1,4-dichloro-2-butene is added drop-wise.

8. The method of claim 3, wherein the molar ratio of 1,4-bis-dimethylamino-2-butene to triethanolamine is from about 10:1 to about 1:5.

9. The method of claim 3, wherein the molar ratio of triethanolamine to acid in said first portion is from about 10:1 to about 1:10.

10. The method of claim 3, wherein the molar ratio of triethanolamine to acid in said second portion is from about 10:1 to about 1:100.

11. The method of claim 3, wherein the molar ratio of triethanolamine to acid in said first and second portions is from about 5:1 to about 1:5.

12. The solution of claim 3, wherein the reaction temperature is from about 70° C. to about 90° C.

13. The solution of claim 3, wherein the reaction time is from about 1 hour to about 40 hours.

* * * * *